United States Patent
Fugerer et al.

(10) Patent No.: US 12,137,960 B2
(45) Date of Patent: Nov. 12, 2024

(54) SURGICAL SYSTEM WITH ADAPTIVE ASPIRATION FLOW CONTROL

(71) Applicant: ARTHREX, INC., Naples, FL (US)

(72) Inventors: Robert Fugerer, Lutz, FL (US); Edwin Floyd, Naples, FL (US); Kenneth Adams, Naples, FL (US)

(73) Assignee: Arthrex, Inc., Naples, FL (US)

( * ) Notice: Subject to any disclaimer, the term of this patent is extended or adjusted under 35 U.S.C. 154(b) by 478 days.

(21) Appl. No.: 17/330,054

(22) Filed: May 25, 2021

(65) Prior Publication Data

US 2022/0378491 A1 Dec. 1, 2022

(51) Int. Cl.
*A61B 18/12* (2006.01)
*A61B 17/00* (2006.01)
(Continued)

(52) U.S. Cl.
CPC .............. *A61B 18/12* (2013.01); *A61B 17/32* (2013.01); *A61B 17/320016* (2013.01);
(Continued)

(58) Field of Classification Search
CPC .......... A61B 18/12; A61B 2018/00714; A61B 2018/00744; A61B 2018/00791;
(Continued)

(56) References Cited

U.S. PATENT DOCUMENTS 4,345,192 A 8/1982 Kohzai et al.
4,705,038 A 11/1987 Sjostrom et al.
(Continued)

FOREIGN PATENT DOCUMENTS

CN 109303592 2/2019
JP 2015097857 5/2015
(Continued)

OTHER PUBLICATIONS

"Design and characterization of a debriding tool in robot-assisted treatment of osteolysis"; Farshid Alambeigi et al.; May 2016, https://www.researchgate.net/profile/Farshid_Alambeigi/publication/30388624T_Design_and_characterization_of_a_debriding_tool_in_robot-assisted_treatment_of_osteolysis/links/59dedd130f7e9bcfab246350/Design-and-characterization-of-a-debriding-tool-in-robot-assisted-treatment-of-osteolysis.pdf.
(Continued)

*Primary Examiner* — Robert A Lynch
(74) *Attorney, Agent, or Firm* — Greenberg Traurig, LLP; Michael K. Dixon

(57) ABSTRACT

An adaptive flow rate control system for a surgical device, whereby the control system includes one or more nonintrusive sensors configured to be positioned on an aspiration conduit extending downstream from a handheld surgical device to measure flow and reduce clogging within the aspiration conduit is disclosed. The nonintrusive sensor may provide data to a controller of a handheld surgical device system to enable it to control operation of the handheld surgical device based at least in part on the data from the adaptive flow rate control system to prevent clogging of the aspiration system. The adaptive flow rate control system may also include a clog tracking module and a clog prediction module. The adaptive flow rate control system may include a wireless communication system configured to communicate with other components of a surgical device system and may communicate with a external network and resources on the internet.

41 Claims, 3 Drawing Sheets

(51) Int. Cl.
  *A61B 17/32* (2006.01)
  *A61B 18/00* (2006.01)
  *A61M 1/00* (2006.01)
  *G16H 40/67* (2018.01)
(52) U.S. Cl.
  CPC .............. *A61M 1/74* (2021.05); *G16H 40/67* (2018.01); *A61B 2017/00084* (2013.01); *A61B 2018/00744* (2013.01); *A61B 2018/00791* (2013.01); *A61B 2018/00863* (2013.01); *A61B 2217/005* (2013.01); *A61B 2218/007* (2013.01)
(58) Field of Classification Search
  CPC ........... A61B 2018/00797; A61B 2018/00863; A61B 2018/0091; A61B 2018/00952; A61B 17/32; A61B 17/320016; A61B 2017/00084; A61B 2217/005; A61B 2218/007; A61M 1/74; A61M 1/741; A61M 1/7411; A61M 1/742; A61M 1/743; A61M 1/76; A61M 1/77; A61M 1/774; A61M 1/80; G16H 40/67
  See application file for complete search history.

(56) References Cited

U.S. PATENT DOCUMENTS

| | | |
|---|---|---|
| 4,867,155 A | 9/1989 | Isaacson |
| 4,995,877 A | 2/1991 | Ams et al. |
| 5,030,900 A | 7/1991 | Kono |
| 5,411,472 A * | 5/1995 | Steg, Jr. ................ A61M 60/43 604/257 |
| 5,602,449 A | 2/1997 | Kruse |
| 5,632,759 A | 5/1997 | Rexroth |
| 5,669,921 A | 9/1997 | Berman et al. |
| 6,743,245 B2 | 6/2004 | Lobdell |
| 7,438,705 B2 | 10/2008 | Karpowicz et al. |
| 7,510,542 B2 | 3/2009 | Blight |
| 7,717,931 B2 | 5/2010 | Himes |
| 7,758,538 B2 | 7/2010 | Boukhny et al. |
| 7,998,157 B2 | 8/2011 | Culp et al. |
| 8,226,677 B2 | 7/2012 | Kauker et al. |
| 8,262,603 B2 | 9/2012 | Shener et al. |
| 8,409,235 B2 | 4/2013 | Rubin |
| 9,028,398 B2 | 5/2015 | Kumar et al. |
| 9,050,123 B2 | 6/2015 | Krause et al. |
| 9,233,193 B2 | 1/2016 | Truckai et al. |
| 9,295,477 B2 | 3/2016 | Schneider et al. |
| 9,308,315 B2 | 4/2016 | Stubkjaer et al. |
| 9,370,611 B2 | 6/2016 | Ross et al. |
| 9,451,977 B2 | 9/2016 | Schmitz et al. |
| 9,456,872 B2 | 10/2016 | Hendrick et al. |
| 9,511,184 B2 | 12/2016 | Woolford et al. |
| 9,737,362 B2 | 8/2017 | Germain et al. |
| 9,814,484 B2 | 11/2017 | Schmitz et al. |
| 9,855,383 B2 | 1/2018 | Shener et al. |
| 9,883,885 B2 | 2/2018 | Hendrick et al. |
| 9,907,563 B2 | 3/2018 | Germain et al. |
| 9,999,466 B2 | 6/2018 | Germain et al. |
| 10,064,644 B2 | 9/2018 | Schmitz et al. |
| 10,137,034 B2 | 11/2018 | Heeren |
| 10,213,246 B2 | 2/2019 | Toth et al. |
| 10,335,180 B2 | 7/2019 | Johnson et al. |
| 10,383,691 B2 | 8/2019 | Hendrick et al. |
| 10,405,924 B2 | 9/2019 | Bowe |
| 10,485,613 B2 | 11/2019 | Hendrick et al. |
| 10,595,882 B2 | 3/2020 | Parfett et al. |
| 2001/0031976 A1* | 10/2001 | Lobdell ............... A61F 9/00763 606/171 |
| 2003/0187390 A1* | 10/2003 | Bates .................. A61M 1/7415 604/9 |
| 2007/0060915 A1* | 3/2007 | Kucklick ............. A61B 18/148 606/1 |
| 2011/0137231 A1 | 6/2011 | Sorensen et al. |
| 2016/0331876 A1* | 11/2016 | Smith ..................... A61M 1/74 |
| 2017/0151092 A1* | 6/2017 | Raney ..................... A61M 1/77 |
| 2017/0367885 A1* | 12/2017 | Bourne .................. A61M 1/80 |
| 2019/0143010 A1 | 5/2019 | Gaspredes et al. |
| 2019/0201082 A1 | 7/2019 | Shelton et al. |
| 2019/0201083 A1 | 7/2019 | Shelton et al. |
| 2019/0201085 A1 | 7/2019 | Shelton et al. |
| 2019/0223898 A1 | 7/2019 | Curtin et al. |
| 2020/0054356 A1 | 2/2020 | Miller et al. |
| 2020/0289722 A1* | 9/2020 | Culbert ............ A61B 17/32037 |
| 2021/0128815 A1 | 5/2021 | Byrne et al. |

FOREIGN PATENT DOCUMENTS

| | | |
|---|---|---|
| WO | 2007/013986 | 2/2007 |
| WO | 2017095679 | 6/2017 |

OTHER PUBLICATIONS

"Tissue model and preliminary analysis of microdebriders used in functional endoscopic sinus surgery"; Sandeep P. Dave et al.; Jun. 1, 2005, htlp://citeseerx.ist.psu.edu/viewdoc/download?doi=10.1.1.930.8847&rep=rep1&type=pdf.

OCCAM MD, "Stryker CORE System Console and Handpiece Benchmarking Report," Dated Nov. 30, 2015, document of 122 pages.

Chen et al., "A review on surgical instruments of knee arthroscopic debridement and total hip arthroplasty," 3rd CIRP Conference on BioManufacturing, 2017, pp. 291-298.

Stryker, "Powered Instrument Driver, REF 5400-50," 2005, document of 37 pages.

Smith & Nephew, "Dyonics Power Shaver System," 2005, document of 52 pages.

Smith & Nephew, "Dyonics Power II Shaver System; Dyonics PowerMax Elite Handpiece," 2012, document of 7 pages.

U.S. Patent and Trademark Office; PCT International Search Report, issued in connection to international application No. PCT/US22/30885; Aug. 24, 2022; 12 pages; US.

U.S. Patent and Trademark Office; PCT Written Opinion of the International Searching Authority, issued in connection to international application No. PCT/US22/30885; Aug. 24, 2022; 8 pages; US.

* cited by examiner

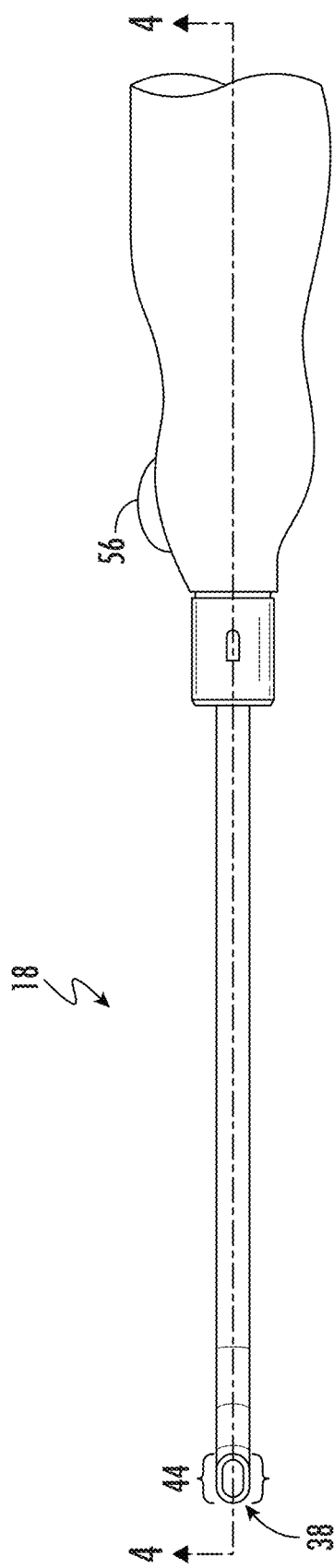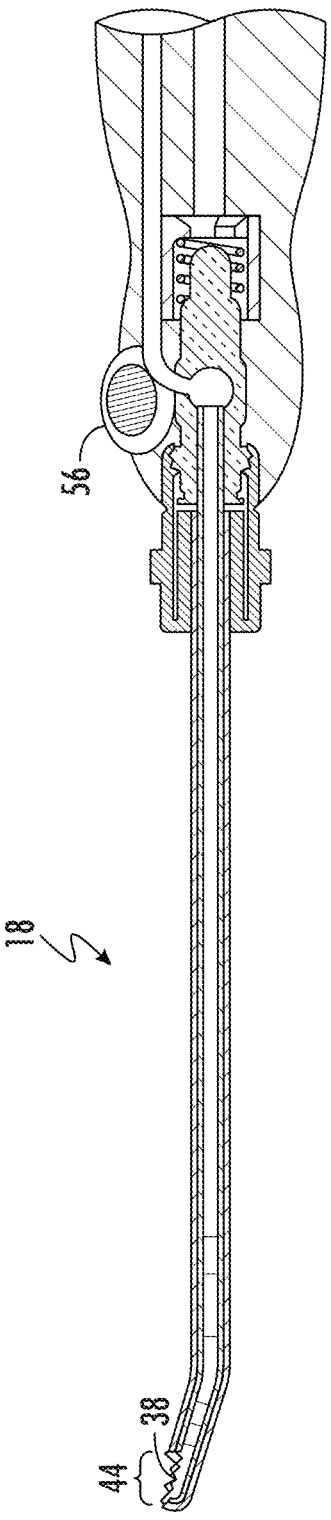
FIG. 3
FIG. 4

SURGICAL SYSTEM WITH ADAPTIVE ASPIRATION FLOW CONTROL

BACKGROUND

The disclosure relates generally to aspiration systems for handheld, rotary medical devices, and more particularly, to operational monitoring systems of aspiration systems servicing handheld surgical devices.

Handheld rotary medical devices include working ends, which are often shavers or burrs, that are configured for the removal of hard or soft tissue from a patient's body. Many of these devices are configured to remove soft tissue. Aspiration systems remove fluids and tissue from a surgical site within a patient. Conventional aspiration systems do not directly measure flow rates but assume flow rates based on the speed of operation of an aspiration pump within the aspiration system. However, operation of the aspiration pump and knowing the speed of the aspiration pump does not provide actual knowledge of aspiration fluids within the aspiration system. Many handheld devices are configured to pass aspiration fluids past a working elements and through the devices for cooling. Tissue and other materials from a surgical site in a patient can cause the aspiration conduit to clog, which can cause overheating of the handheld device and the aspiration pump.

SUMMARY

An adaptive flow rate control system for a surgical device, whereby the control system includes one or more nonintrusive sensors configured to be positioned on an aspiration conduit extending downstream from a handheld surgical device to measure flow and reduce clogging within the aspiration conduit is disclosed. The nonintrusive sensor may provide data to enable an aspiration system controller to control an aspiration pump or a device controller of a handheld surgical device system to control a handheld surgical device, or both, based, at least in part, on the data from the adaptive flow rate control system to prevent clogging of the aspiration system. The adaptive flow rate control system may also include a clog tracking module to track boluses and clogs flowing through the aspiration conduit and a clog prediction module to predict the occurrence of clogs forming in the aspiration conduit. The adaptive flow rate control system may include a wireless communication system configured to communicate with other components of a surgical system and may communicate with a external network and resources on the internet.

The adaptive flow rate control system may include one or more nonintrusive sensors configured to be positioned on an aspiration conduit extending downstream from a working element in the handheld surgical device, which may be, but is not limited to being, a shaver or an RF probe. In at least one embodiment, the nonintrusive sensor may be removably attached to the aspiration conduit and, in at least one embodiment, may snap onto an outer surface of the aspiration conduit via an interference fit or the like. The nonintrusive sensor may provide data to an aspiration system controller, thereby enabling the aspiration system controller to control the aspiration pump based, at least in part, on the data generated by the nonintrusive sensor, or may provide data to a device controller, thereby enabling the device controller to control the handheld surgical device based, at least in part, on the data generated by the nonintrusive sensor, or both. The nonintrusive sensor may be, but is not limited to being, an ultrasonic sensor, a wireless sensor or a battery powered sensor, which may be rechargeable. In at least one embodiment, the nonintrusive sensor may be positioned within the handheld surgical device to detect aspiration fluid flow within the handheld surgical device thereby monitoring cooling of the handheld surgical device by the aspiration system such that the handheld surgical device may be safely operated at high speeds.

The adaptive flow rate control system may be incorporated within a surgical system including a handheld surgical device with a working element, and an aspiration system with an aspiration pump and an aspiration conduit extending from the handheld surgical device to the aspiration pump. The adaptive flow rate control system may include one or more nonintrusive sensors positioned on the aspiration whereby the nonintrusive sensor is in communication with a controller that controls operation of the aspiration pump. The aspiration pump may be configured to control suction via aspiration pump operation based, at least in part, on data provided by the nonintrusive sensor. The adaptive flow rate control system may be configured to process the data obtained with one or more of the nonintrusive sensors via artificial intelligence and other appropriate protocols.

The nonintrusive sensor may be configured to sense density of fluid flowing within the aspiration conduit. The nonintrusive sensor may also be configured to sense fluid velocity flowing within the aspiration conduit such as via doppler effect with radio waves, sounds waves or the like. The nonintrusive sensor may be configured to sense temperature of a material flowing through the at least one aspiration conduit. The adaptive flow rate control system may also include a camera configured to capture images of matter flowing within the aspiration conduit. The captured image data may be processed, such as, but not limited to, via artificial intelligence and other imaging processing systems, to determine the nature of particulates in the material within the aspiration conduit, such as, but not limited to, blood, bone, tissue, metal, et cetera.

The nonintrusive sensor may be positioned at a potential blockage location in the aspiration conduit to enable the adaptive flow rate control system to detect a bolus in the aspiration conduit. In particular, the nonintrusive sensor may be placed at various potential trouble spots along the aspiration conduit, such as, but not limited to, locations of changes of inside diameters of the aspiration conduit, such as connections between two different sections, and the like, where material can get caught up. The nonintrusive sensor may be positioned upstream from a potential trouble spot in the aspiration conduit to enable the adaptive flow rate control system to detect a bolus before the bolus stops flow through the aspiration conduit and to make adjustments to prevent blockage of the aspiration conduit. The adaptive flow rate control system may be configured to determine bolus speed, density and location based on input from the nonintrusive sensor.

The adaptive flow rate control system may also include a clog tracking module configured to track a location of a bolus or a clog, or both within the aspiration conduit. The clog tracking module may include a plurality of nonintrusive sensors positioned along the aspiration conduit for tracking a location of a bolus or a clog within the aspiration conduit. The clog tracking module may generate results viewable to a user in any desirable user interface.

The adaptive flow rate control system may include a clog prediction module configured to predict a future location of a clog based at least, in part, on data from the nonintrusive sensor. The clog prediction module may be configured to predict clogging within the aspiration conduit based on density values determined by the adaptive flow rate control system from concentration data generated by the nonintrusive sensor. The clog prediction module may generate results viewable to a user in any desirable user interface.

The adaptive flow rate control system may include a user input receiver configured to receive one or more inputs from a user to actuate a clog removal function whereby the adaptive flow rate control system is configured to actuate the aspiration pump to clear a blocked line. In at least one embodiment, the a user may provide a single input, such as, but not limited to being, a single actuation to actuate the aspiration pump to clear a blocked line. In at least one embodiment, actuation of the clog removal function causes an increase in speed of the aspiration pump to create a greater vacuum to prevent a blockage or remove a blockage. The adaptive flow rate control system may be configured to be in communication with the device controller to close a window at the working element in the handheld surgical device to further increase the vacuum within the aspiration conduit. Closing the window at the working element increases the vacuum within the aspiration conduit and creates a large flush within the aspiration system.

In at least one embodiment, the adaptive flow rate control system may include a roller valve positioned in the handheld surgical device enabling a user to control aspiration through the aspiration conduit via rotational movement of the roller valve. The adaptive flow rate control system may be configured to sense the aspiration reduction caused by movement of the roller valve and send a signal to the aspiration pump to increase in speed to create a greater vacuum.

The adaptive flow rate control system may include a communication system configured to receive data from the nonintrusive sensor and transmit the data to one or more control systems, such as, but not limited to, an aspiration controller configured to control operation of the aspiration pump, a device controller configured to control operation of the handheld surgical device, and the like. In particular, the communication system may transmit to or receive data from, or both, one or more nonintrusive sensors, one or more handheld surgical devices, one or more aspiration controllers, one or more device controllers and one or more external networks, such as, but not limited to a remote server, the internet, a cloud storage platform and AMAZON WEB SERVICES. The communication system is configured to communicate via wired or wireless communications, such as, but not limited to, radio frequency signal, such as, but not limited to BLUETOOTH. The communication system may be configured to receive and transmit data including, but not limited to, aspiration fluid flow velocity, aspiration fluid flow density, aspiration fluid flow temperature and aspiration fluid pressure within the aspiration conduit. The adaptive flow rate control system may also include a data bus placing the at least one nonintrusive sensor in communication with the aspiration controller, device controller and other devices and systems.

An advantage of the adaptive flow rate control system is that the system includes nonintrusive sensors which sense various parameters of the material being transported within the aspiration conduit and away from the working element of the handheld surgical device without potentially clogging the aspiration conduit.

Another advantage of the adaptive flow rate control system is that the nonintrusive sensors may be releasably snapped onto the outer surface of the aspiration conduit at any location along the length of the aspiration conduit. As such, the nonintrusive sensors may be repositioned along the length of the aspiration conduit to increase the effectiveness of the sensors to detect clogs and boluses.

Yet another advantage of the adaptive flow rate control system is that the system may include clog tracking module with a plurality of nonintrusive sensors positioned along the aspiration conduit for tracking a location of clogs or boluses within the aspiration conduit.

Another advantage of the adaptive flow rate control system is that the system may include one or more nonintrusive sensors placed upstream of clogging points so the system can identify a clog before it reaches a clogging point and make adjustments to the aspiration system and working element to ensure the aspiration conduit doesn't become clogged.

Still another advantage of the adaptive flow rate control system is that the system may predict the occurrence of a clog and make adjustments to the aspiration system and working element to ensure the aspiration conduit doesn't become clogged.

These and other embodiments are described in more detail below.

BRIEF DESCRIPTION OF THE DRAWINGS

FIG. 2 is an exploded side of the shaver shown in FIG. 1.

FIG. 3 is a partial assembled top view of a handheld surgical device shown in FIG. 2.

FIG. 4 is cross-sectional partial side view of the handheld surgical device taken as section line 4-4 in FIG. 3.

DETAILED DESCRIPTION

Figure 1:
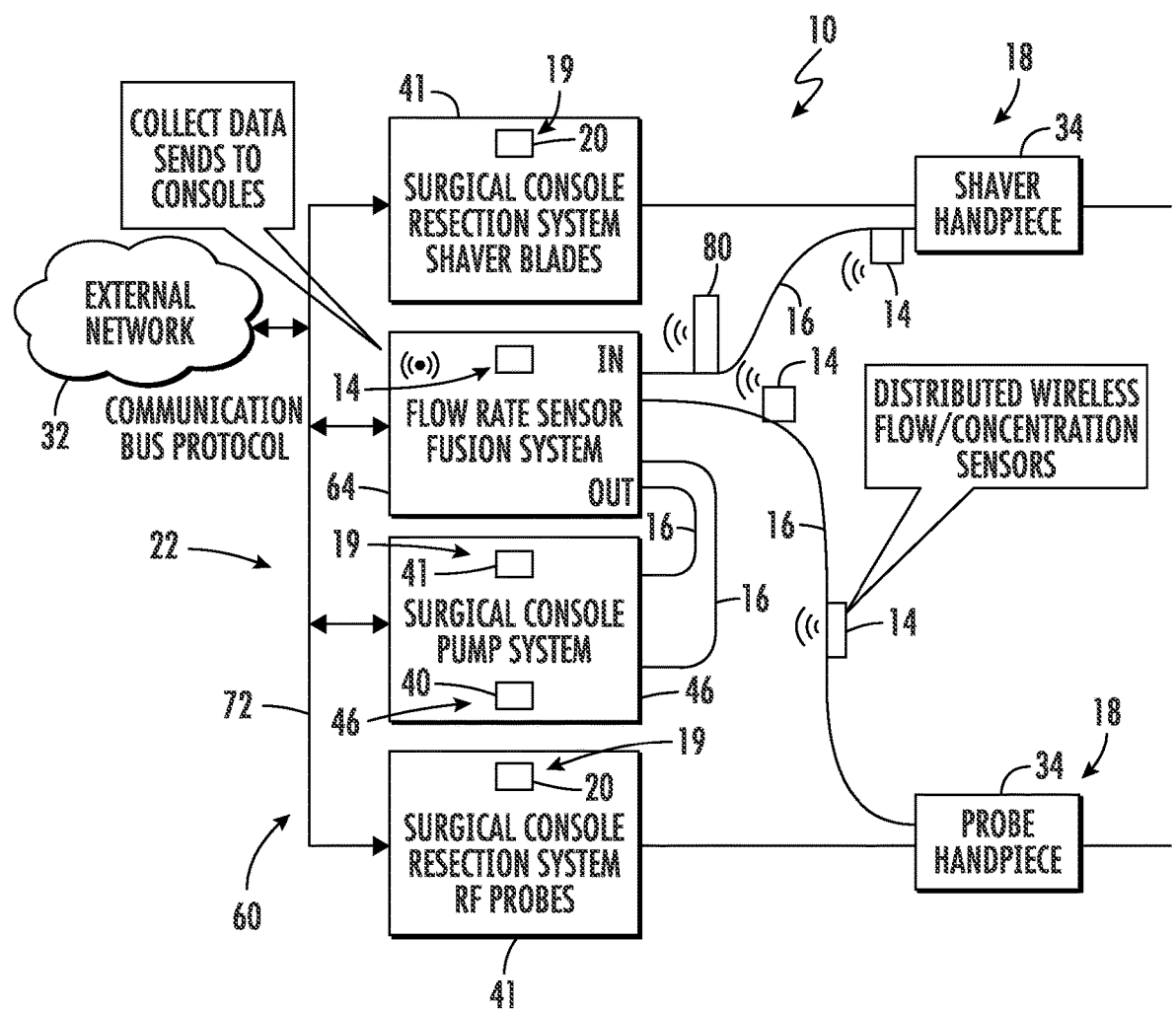
FIG. 1 is a schematic diagram of the adaptive flow rate control system.

As shown in FIGS. 1-4, an adaptive flow rate control system 10 for a handheld surgical device system 22, whereby the adaptive flow rate control system 10 includes one or more nonintrusive sensors 14 configured to be positioned on an aspiration conduit 16 extending downstream from a handheld surgical device 18 to measure flow and reduce clogging within the aspiration conduit 16 is disclosed. The nonintrusive sensor 14 may provide data to one or more controllers 19 of the adaptive flow rate control system 10 or a handheld surgical device system 22, or both, such that the controller 19 can operate based, at least in part, on the data from the nonintrusive sensor 14 to prevent clogging of the aspiration system 24. In particular, the nonintrusive sensor 14 may provide data to enable an aspiration system controller 41 to control an aspiration pump 40 or a device controller 20 of a handheld surgical device system 22 to control a handheld surgical device 18, or both, based, at least in part, on the data from the adaptive flow rate control system 10 to prevent clogging of the aspiration system 24. The adaptive flow rate control system 10 may also include a clog tracking module 26 to track boluses and clogs flowing through the aspiration conduit 16 and a clog prediction module 28 to predict the occurrence of clogs forming in the aspiration conduit 16. The adaptive flow rate control system 10 may include a wireless communication system configured to communicate with other components of a handheld surgical device system 22 and may communicate with an external network 32 and resources on the internet.

Figure 2:
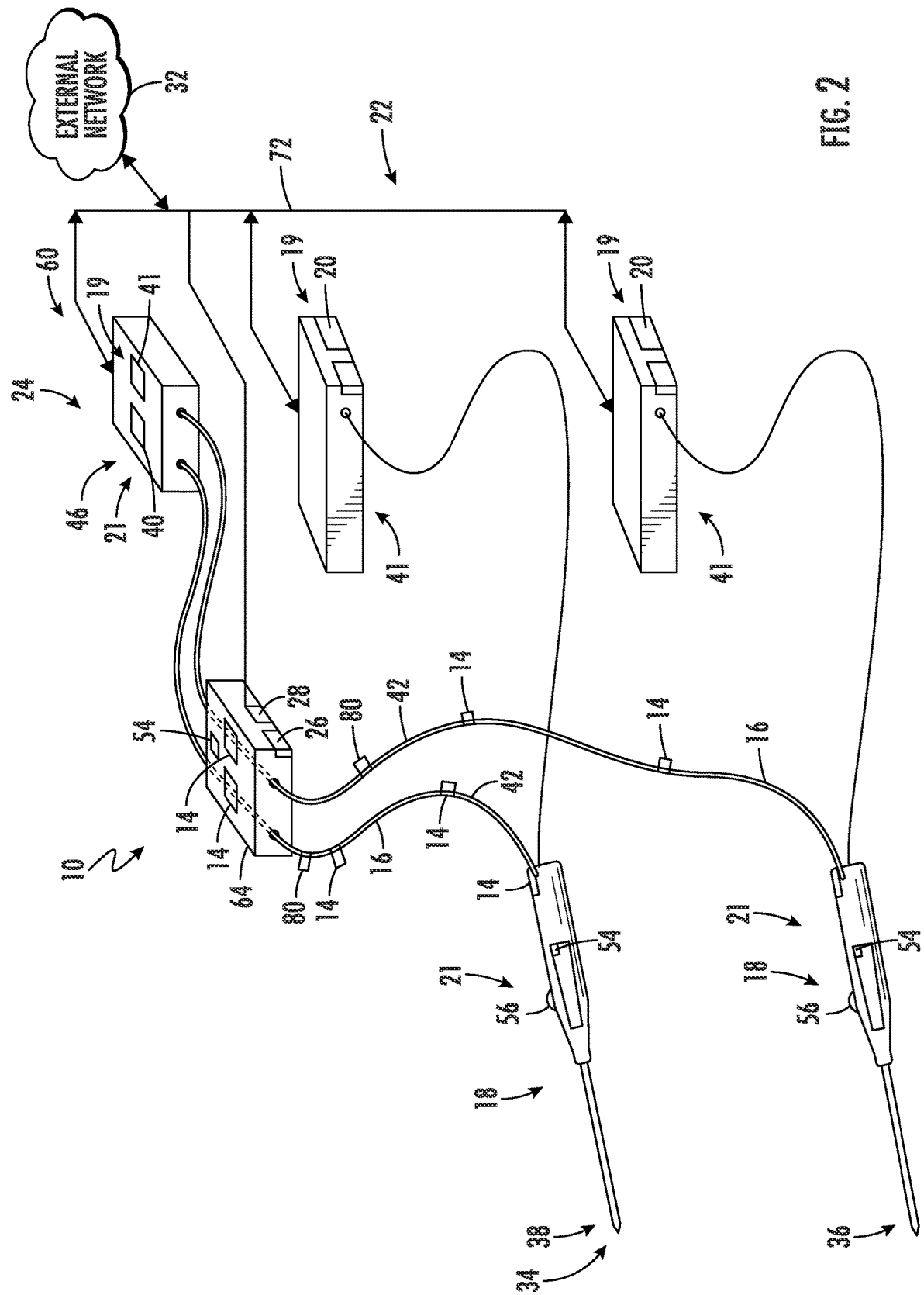
FIG. 2 is a perspective view of the adaptive flow rate control system.

In at least one embodiment, as shown in FIGS. 1 and 2, the adaptive flow rate control system 10 may be configured for providing data to one or more controllers 19 of the adaptive flow rate control system 10 or a handheld surgical device system 22, or both. The controllers 19 may be, but are not limited to being one or more aspiration system controllers 41, one or more device controllers 20, other controllers, or any combination thereof. The one or more controllers 19 may be configured to control one or more components 21 of the adaptive flow rate control system 10, which includes, but is not limited to, components 21 of the aspiration system 24 and components 21 of the handheld surgical device system 22. The components 21 of the aspiration system 24 may include, but are not limited to, one or more aspiration pumps 40. The components 21 of the handheld surgical device system 22 may include, but are not limited to, one or more handheld surgical devices 18.

The device controller 20 of the handheld surgical device 18 may be incorporated within a console or otherwise positioned. The handheld surgical device 18 may be any handheld device 18, such as, but not limited to a shaver 34, an electrosurgical probe 36, such as an RF probe, and the like, with any appropriate working element 38, such as, but not limited to a shaver, a burr, a blade and the like. In at least one embodiment, the handheld surgical device system 22 may have a plurality of handheld surgical devices 18. The plurality of handheld surgical devices 18 may be controlled via a single device controller 20 or may each be controlled with its own dedicated device controller 20.

The aspiration system 24 may include one or more aspiration pumps 40 and an aspiration conduit 16 extending from the handheld surgical device 18 to the aspiration pump 40. The aspiration pump 40 may be configured to aspirate material from a surgical site into the aspiration conduit 16. The aspiration pump 40 may be controlled via one or more aspiration system controllers 41. Alternatively, the aspiration pump 40 may be controlled via the same device controller 20 that controls the handheld surgical device 18 or a separate controller. The nonintrusive sensor 14 may be in communication with the aspiration system controller 41 that controls operation of the aspiration pump 40 such that the aspiration pump 40 is configured to control suction within the aspiration system 24 via aspiration pump operation based, at least in part, on data provided by the nonintrusive sensor 14. The aspiration system controller 41 may be contained within an aspiration console, included within a surgical device console 46 or otherwise positioned.

The adaptive flow rate control system 10 may include one or more nonintrusive sensors 14 configured to be positioned on an aspiration conduit 16 downstream of the working element 38. The nonintrusive sensor 14 may be, but is not limited to being, an ultrasonic sensor or other appropriate sensor. The nonintrusive sensor 14 may be a wired or wireless sensor. The wireless nonintrusive sensor 14 provides flexibility such that the sensor 14 may be positioned in any desired positioned along the aspiration conduit 16 without accounting for wires possibly limiting mounting locations. The nonintrusive sensor 14 may be a battery powered sensor, which may or may not be rechargeable. The nonintrusive sensor 14 may also be powered via a surgical operating room power source, such as, but not limited to a municipal power source.

In at least one embodiment, the nonintrusive sensor 14 may be positioned on an aspiration conduit 16 downstream of the handheld surgical device 18. The nonintrusive sensor 14 may be positioned on the aspiration conduit 16 between the handheld surgical device 18 and the aspiration pump 40. The nonintrusive sensor 14 may be configured such that the sensor 14 snaps onto an outer surface 42 of the aspiration conduit 16. The aspiration conduit 16 may be formed from, but is not limited to, flexible tubing. In at least one embodiment, the nonintrusive sensor 14 may snap onto the tubing forming the aspiration conduit 16. As such, the nonintrusive sensor 14 may be releaseably attached to the aspiration conduit 16, thereby enabling the nonintrusive sensor to be removed altogether or to be repositioned to another location on the tubing forming the aspiration conduit 16 to provide better results.

In another embodiment, the nonintrusive sensor 14 may be positioned on an aspiration conduit 16 within the handheld surgical device 18. The nonintrusive sensor 14 may be positioned in the handheld surgical device 18 for protection of the handheld surgical device 18. Aspiration fluids removed from a surgical site via one or more aspiration conduits 16 also function to cool the handheld surgical device 18 by removing heat generated by high speed operation of the handheld surgical device 18. The nonintrusive sensor 14 in the handheld surgical device 18 may function to confirm the flow of aspiration fluids in the aspiration conduit 16 to confirm that the handheld surgical device 18 is being adequately cooled when the handheld surgical device 18 is operated at high speeds.

The nonintrusive sensor 14 may provide data to one or more aspiration system controllers 41 of the aspiration system 24, thereby enabling the aspiration system controllers 41 to control operation of the aspiration pump 40 based, at least in part, on the data. The nonintrusive sensor 14 may provide data to one or more device controllers 20 of a handheld surgical device system 22, thereby enabling the controller 20 to control operation of the handheld surgical device 18 based, at least in part, on the data. The nonintrusive sensor 14 may provide data to the aspiration system controller 41 or the device controller 20, or both. The nonintrusive sensor 14 may provide early warnings of abnormal flow rate and no flow conditions. In particular, the nonintrusive sensor 14 may provide early warnings of no flow conditions to the device controller 20, thereby enabling the device controller 20 to limit speed or cease operation of an attached handheld surgical device 18 to prevent overheating of the device 18.

The nonintrusive sensor 14 may be permanently or removeably positioned at a potential blockage location in the aspiration conduit 16 to enable the adaptive flow rate control system to detect a bolus or a clog in the aspiration conduit 16. The nonintrusive sensor 14 may be placed at various potential trouble spots along the aspiration conduit 16, such as, but not limited to, locations of changes of inside diameters of the aspiration conduit 16, such as connections between two different sections, and the like, where material can get held up and form clogs. The nonintrusive sensor 14 may be positioned upstream from a potential trouble spot in the aspiration conduit 16 to enable the adaptive flow rate control system 10 to detect a bolus or clog before the bolus or clog stops flow through the aspiration conduit 16. The aspiration system controller 41 may be configured to make adjustments in operation of the aspiration system 24 to accommodate a bolus or clog traveling in the aspiration conduit 16, and the device controller 20 may be configured to make adjustments in operation of the handheld surgical device 18 to accommodate a bolus or clog traveling in the aspiration conduit 16. In at least one embodiment, the nonintrusive sensor 14 may be positioned upstream a distance such as, but not limited to, twelve inches, or other appropriate or desired distance from a potential trouble spot in the aspiration conduit 16. The data from the nonintrusive sensor 14 may enable the adaptive flow rate control system 10 to determine bolus speed, density and location.

The adaptive flow rate control system 10 may also include a clog tracking module 26 configured to track a location of a clog or bolus within the aspiration conduit 16. The clog tracking module 26 may include one or more nonintrusive sensors 14, and in at least one embodiment, include a plurality of nonintrusive sensors 14 positioned along the aspiration conduit 16 for tracking a location of a clog within the aspiration conduit 16. The clog tracking module 26 may generate results viewable to a user in any desirable user interface. The user may provide input to control operation of the aspiration pump 40 or the one or more handheld surgical devices 18, or any combination thereof. Also, the adaptive flow rate control system 10 may automatically adjust operation of the aspiration pump 40 or the one or more handheld surgical devices 18 or any combination thereof to account for the clog or bolus within the aspiration conduit 16 to prevent clogging the aspiration conduit.

The adaptive flow rate control system 10 may also include a clog prediction module 28 configured to predict a future location of a clog or bolus based, at least in part, on data from the nonintrusive sensor 14. The clog prediction module 28 may be configured to provide early warnings of abnormal flow rate and high concentrations of debris so that the adaptive flow rate control system 10 can alert a user, the aspiration system controller 41 or the device controller, or any combination thereof, thereby enabling appropriate action to be taken to prevent clogging. The clog prediction module 28 may be configured to predict clogging within the aspiration conduit 16 based on density values determined by the adaptive flow rate control system 10 fluid from concentration data generated by the nonintrusive sensor 14. The clog prediction module 28 may generate results viewable to a user in any desirable user interface. The user may provide input to control operation of the aspiration pump 40 or the one or more handheld surgical devices 18, or any combination thereof. Also, the adaptive flow rate control system 10 may automatically adjust operation of the aspiration pump 40 or the one or more handheld surgical devices 18 or any combination thereof to account for the predicted clog within the aspiration conduit 16 to prevent clogging the aspiration conduit.

The adaptive flow rate control system 10 may communicate with the aspiration system controller 41 or the device controller 20, or both, to indicate existence of a clog, beginning formation of a clog or reduced aspiration flow, or any combination thereof. the aspiration system controller 41 may then operate the working element 38 or the device controller 20 may operate the working element 38, or both, to eliminate the clog and restore full, unimpeded flow to the aspiration conduit 16. In at least one embodiment in which the working element 38 is a shaver aligned with an opening in an outer housing to form a cutting window 44, as shown in FIGS. 3 and 4, the device controller 20 may operate the working element 38 to open and close the cutting window 44 at the working element 38 to create a pumping action in a handheld surgical device 18. The device controller 20 may be configured to send a signal to change a rotational speed or oscillation speed based on the data from the nonintrusive sensor 14 in addition to the device controller 20 changing the window opening amount and length of time the aspiration pump 40 is at the same speed to unclog the aspiration conduit 16. The aspiration system controller 41 may be operated to use negative pressure priming and relief to unclog the aspiration conduit 16.

In at least one embodiment, the adaptive flow rate control system 10 may include a user input receiver 54 configured to receive one or more inputs from a user to cause the system 10 to change operating conditions to clear the obstructions in the aspiration conduit 16. In at least one embodiment, a user, such as, but not limited to, a surgeon, may actuate a single button, which may be on the handheld surgical device 18, surgical pump console 46 or elsewhere, to cause the system 10 to change operating conditions to clear the obstructions in the aspiration conduit 16. The adaptive flow rate control system 10 may be configured to actuate a clog removal function whereby the adaptive flow rate control system 10 is configured to actuate the aspiration pump 40 to increase in speed to create a greater vacuum. The adaptive flow rate control system 10 may be configured to be in communication with the controller 20 to close a window 44, as shown in FIGS. 3 and 4, at the working element 38 to further increase the vacuum within the aspiration conduit 16. Closing the window 44 at the working element 38 increases the vacuum within the aspiration conduit 16 and creates a large flush within the aspiration system 24. In at least one embodiment, the user input receiver 54 may be a roller valve 56, as shown in FIGS. 3 and 4, positioned in the handheld surgical device 18 enabling a user to control aspiration through the aspiration conduit 16 via rotational movement of the roller valve 56, whereby the adaptive flow rate control system 10 is configured to sense the aspiration increase caused by movement of the roller valve 56 and send a signal to the aspiration pump 40 to increase in speed to create a greater vacuum.

The nonintrusive sensor 14 may be configured to sense a number of parameters of the fluid and material within the aspiration conduit 16. For example, the nonintrusive sensor 14 may be configured to sense density of fluid flowing within the aspiration conduit 16. The nonintrusive sensor 14 may also be configured to sense fluid velocity flowing within the aspiration conduit 16. In at least one embodiment, the nonintrusive sensor 14 may operate via doppler effect with radio waves or sounds waves. The adaptive flow rate control system 10 may also include one or more nonintrusive sensors 14 configured to sense temperature of a material flowing through the aspiration conduit 16. In at least one embodiment, the adaptive flow rate control system 10 may be configured to bounce RF off the aspiration conduit 16 and infer temperature of fluid inside aspiration conduit 16. In another embodiment, the adaptive flow rate control system 10 may use infrared imaging as a heat sensor. The adaptive flow rate control system 10 may determine temperature of material flowing through the aspiration conduit 16 via other ways as well. In at least one embodiment, the adaptive flow rate control system 10 may use a frame rate to identify a flow rate of particulates within the aspiration conduit 16. The adaptive flow rate control system 10 may also include one or more nonintrusive sensors 14 configured to sense pressure.

The adaptive flow rate control system 10 may include a nonintrusive sensor 14 that may be an optical sensor 80. In at least one embodiment, the optical sensor 80 may be a camera 80, such as, but not limited to a small camera such as a camera used in smartphones, thermal imaging, and the like, configured to capture images of matter flowing within the aspiration conduit 16. The image data captured may be processed, such as, but not limited to, via artificial intelligence and other imaging processing, to determine the nature of particulates in the material within the aspiration conduit, such as, but not limited to, blood, bone, tissue, metal, et cetera. The optical sensor 80 may be configured to capture multiple images and transmit the images and time stamps to one or more controllers 19 to determine a speed of the material flowing within the aspiration conduit 16. The adaptive flow rate control system 10 may include multiple optical sensors 80 positioned a known distance apart and configured to capture multiple images and transmit the images and time stamps to one or more controllers 19 to determine a speed of the material flowing within the aspiration conduit 16 by tracking a location of a known piece of material flowing within the aspiration conduit 16 past the two or more optical sensors 80.

The adaptive flow rate control system 10 may include a communication system 60 configured to receive data at the aspiration system control 41 from the nonintrusive sensor 14 and transmit the data to the device controller 20, external networks, other systems and any combination thereof to control operation of one or more components of the handheld surgical device system 22, such as, but not limited to, handheld surgical device 18. The communication system 60 may be configured to communicate via wireless communications, such as, but not limited to, radio frequency signals, including, but not limited to, BLUETOOTH. The nonintrusive sensor 14 may communicate wirelessly with a handheld surgical device 18, the aspiration system control 41, the device controller 20 and external networks 32. The communication system 60 may be configured to receive and transmit data including, but not limited to, aspiration fluid flow velocity, aspiration fluid flow density, aspiration fluid flow temperature, aspiration fluid pressure and temperature within the aspiration conduit 16. In at least one embodiment, the adaptive flow rate control system 10 may be configured to transmit data from the nonintrusive sensor 14 to the aspiration system controller 41 that controls the aspiration pump 40, to the device controller 20 that controls the handheld surgical device 18 or to an external network 32, or any combination thereof. The external network 32 may be one or more remote servers, the internet, a cloud storage platform, AMAZON WEB SERVICES, and other such systems. The adaptive flow rate control system 10 may be configured to send data, such as, but not limited to, aspiration fluid flow velocity, aspiration fluid flow density, aspiration fluid flow temperature, aspiration fluid pressure, temperature and additional data to the external network 32 for analysis, storage and other use.

The adaptive flow rate control system 10 may include an interface housing 64 configured to act as a pass thru for the aspiration conduit 16 between the handheld surgical device 18 and the aspiration pump 40. Such configuration may be usable where only a single nonintrusive sensor 14 is desired. The single nonintrusive sensor 14 may be housed within the interface housing 64. If communications between the nonintrusive sensor 14 and other components is via wireless communications, the interface housing 64 may be a communications hub configured to receive data via wireless communications from one or more nonintrusive sensors 14 and transmit that data to components 21, such as, but not limited to, the aspiration system controller 41, the aspiration pump 40, the device controller 20, the handheld surgical device 18, external networks 32 and other destinations. The interface housing 64 could bundle data from a plurality of nonintrusive sensors 14 and pass that data on to the components 21 such that those components could operate based, at least in part, on the data from the nonintrusive sensors 14.

The adaptive flow rate control system 10 may include a data bus 72 placing one or more nonintrusive sensors 14 in communication with the aspiration system controller 41 and one or more device controllers 20 configured to control one or more handheld surgical devices 18. In at least one embodiment, the data bus 72 may place one or more nonintrusive sensors 14 in communication with a device controller 20 configured to control a shaver 34 and a device controller 20 configured to control an RF probe 36. The data bus 72 may have any appropriate configuration.

During use, the adaptive flow rate control system 10 functions to prevent clogging and if a clogs forms, to clear the line. The one or more nonintrusive sensors 14 may be configured to send data to the aspiration system controller 41 that controls the aspiration pump 40, to the device controller 20 that controls the handheld surgical device 18 or to an external network 32, or any combination thereof so that a user or one or more of the controllers may take corrective action to prevent clog formation or to clear a line.

The foregoing is provided for purposes of illustrating, explaining, and describing embodiments of the disclosed devices.

We claim:

1. An adaptive flow rate control system for a surgical device, comprising:
   at least one nonintrusive sensor configured to be positioned on an aspiration conduit extending downstream from a handheld surgical device;
   wherein the at least one nonintrusive sensor provides data to at least one controller of the adaptive flow rate control system thereby enabling the at least one controller to control operation of at least one component of the adaptive flow rate control system based, at least in part, on the data provided by the at least one nonintrusive sensor; and
   a clog prediction module configured to predict a future location of a clog based at least in part on data from the at least one nonintrusive sensor.

2. The adaptive flow rate control system of claim 1, wherein the at least one component of the adaptive flow rate control system comprises at least one aspiration system controller configured to control an aspiration pump.

3. The adaptive flow rate control system of claim 1, wherein the at least one component of the adaptive flow rate control system comprises at least one device controller configured to control at least one handheld surgical device.

4. The adaptive flow rate control system of claim 1, wherein the at least one nonintrusive sensor is configured to snap onto an outer surface of the aspiration conduit.

5. The adaptive flow rate control system of claim 1, wherein the at least one nonintrusive sensor is configured to sense density of fluid flowing within the aspiration conduit.

6. The adaptive flow rate control system of claim 1, wherein the at least one nonintrusive sensor is configured to sense fluid velocity flowing within the aspiration conduit.

7. The adaptive flow rate control system of claim 1, wherein the at least one nonintrusive sensor is configured to sense temperature of a material flowing through the at least one aspiration conduit.

8. The adaptive flow rate control system of claim 1, further comprising a clog tracking module configured to track a location of a clog within the aspiration conduit, wherein the clog tracking module comprises a plurality of nonintrusive sensors configured to be positioned along the aspiration conduit for tracking a location of a clog within the aspiration conduit.

9. The adaptive flow rate control system of claim 1, wherein the clog prediction module is configured to predict clogging within the aspiration conduit based on density values determined by the adaptive flow rate control system fluid from concentration data generated by the at least one nonintrusive sensor.

10. The adaptive flow rate control system of claim 1, further comprising a user input receiver configured to receive at least one input from a user to actuate a clog removal function whereby the adaptive flow rate control system is configured to actuate an aspiration pump to increase in speed to create a greater vacuum.

11. The adaptive flow rate control system of claim 1, further comprising an interface housing configured to house the nonintrusive sensor and to receive data via wireless communications from the at least one nonintrusive sensor.

12. The adaptive flow rate control system of claim 1, further comprising a wireless communication system configured to receive data from the at least one nonintrusive sensor and transmit the data to the at least one controller configured to control operation of at least one component of the adaptive flow rate control system.

13. A surgical device system, comprising:
a handheld surgical device with a working element;
an aspiration system comprising an aspiration pump, aspiration system controller and an aspiration conduit extending from the handheld surgical device to the aspiration pump;
an adaptive flow rate control system comprising at least one nonintrusive sensor positioned on the aspiration conduit downstream from the working element of the handheld surgical device;
wherein the at least one nonintrusive sensor is in communication with the aspiration system controller that controls operation of the aspiration pump such that the aspiration pump is configured to control suction within the aspiration conduit via pump operation based, at least in part, on data provided by the at least one nonintrusive sensor; and
wherein the at least one nonintrusive sensor is positioned upstream from a potential trouble spot in the aspiration conduit to enable the adaptive flow rate control system to detect a bolus before the bolus stops flow through the aspiration conduit.

14. The surgical device system of claim 13, wherein the at least one nonintrusive sensor is in communication with at least one device controller that controls the handheld surgical device such that the at least one device controller is configured to control operation of the at least one handheld surgical device based, at least in part, on data provided by the at least one nonintrusive sensor.

15. The surgical device system of claim 13, wherein the at least one nonintrusive sensor is positioned on the aspiration conduit between the handheld surgical device and the aspiration pump.

16. The surgical device system of claim 13, wherein the at least one nonintrusive sensor snaps onto an outer surface of the aspiration conduit.

17. The surgical device system of claim 13, wherein the at least one nonintrusive sensor is positioned within the handheld surgical device.

18. The surgical device system of claim 13, wherein the at least one nonintrusive sensor is positioned at a potential blockage location in the aspiration conduit to enable the adaptive flow rate control system to detect a clog in the aspiration conduit.

19. The surgical device system of claim 13, wherein data from the at least one nonintrusive sensor enables the adaptive flow rate control system to determine fluid velocity.

20. The surgical device system of claim 13, wherein data from the at least one nonintrusive sensor enables the adaptive flow rate control system to determine fluid density.

21. The surgical device system of claim 13, wherein data from the at least one nonintrusive sensor enables the adaptive flow rate control system to determine fluid temperature.

22. The surgical device system of claim 13, wherein the adaptive flow rate control system further comprising a clog tracking module configured to track a location of a clog within the aspiration conduit, wherein the clog tracking module comprises a plurality of nonintrusive sensors positioned along the aspiration conduit for tracking a location of a clog within the aspiration conduit.

23. The surgical device system of claim 13, wherein the adaptive flow rate control system further comprises a user input receiver configured to receive at least one input from a user to actuate a clog removal function whereby the adaptive flow rate control system is configured to actuate the aspiration pump to increase in speed to create a greater vacuum.

24. The surgical device system of claim 13, wherein the adaptive flow rate control system is configured to be in communication with a device controller to close a window at the working element to further increase the vacuum within the aspiration conduit.

25. The surgical device system of claim 13, wherein the adaptive flow rate control system further comprises a roller valve positioned in the handheld surgical device enabling a user to control aspiration through the aspiration conduit via rotational movement of the roller valve and wherein the adaptive flow rate control system is configured to sense the aspiration reduction caused by movement of the roller valve and send a signal to the aspiration pump to increase in speed to create a greater vacuum.

26. The surgical device system of claim 13, wherein the adaptive flow rate control system further comprises an interface housing configured to house the nonintrusive sensor and to receive data via wireless communications from the at least one nonintrusive sensor.

27. The surgical device system of claim 13, wherein the adaptive flow rate control system further comprises a communication system configured to receive data from the at least one nonintrusive sensor and transmit the data to at least one surgical console configured to control operation of at least one component of the system.

28. The surgical device system of claim 27, wherein the communication system is configured to communicate via wireless communications.

29. The surgical device system of claim 13, wherein the adaptive flow rate control system further comprises a data bus placing the at least one nonintrusive sensor in communication with the aspiration system controller.

30. The surgical device system of claim 13, wherein the at least one nonintrusive sensor is a camera configured to capture images of matter flowing within the aspiration conduit.

31. A surgical device system, comprising:
a handheld surgical device with a working element;
an aspiration system comprising an aspiration pump, aspiration system controller and an aspiration conduit extending from the handheld surgical device to the aspiration pump;
an adaptive flow rate control system comprising at least one nonintrusive sensor positioned on the aspiration conduit downstream from the working element of the handheld surgical device;
wherein the at least one nonintrusive sensor is in communication with the aspiration system controller that controls operation of the aspiration pump such that the aspiration pump is configured to control suction within the aspiration conduit via pump operation based, at least in part, on data provided by the at least one nonintrusive sensor; and wherein the adaptive flow rate control system further comprises a clog prediction module configured to predict a future location of a clog based, at least in part, on data from the at least one nonintrusive sensor.

32. The surgical device system of claim 31, wherein the clog prediction module is configured to predict clogging within the aspiration conduit based on density values determined by the adaptive flow rate control system fluid from concentration data generated by the at least one nonintrusive sensor.

33. The surgical device system of claim 31, wherein the at least one nonintrusive sensor is in communication with at least one device controller that controls the handheld surgical device such that the at least one device controller is configured to control operation of the at least one handheld surgical device based, at least in part, on data provided by the at least one nonintrusive sensor.

34. The surgical device system of claim 31, wherein the at least one nonintrusive sensor snaps onto an outer surface of the aspiration conduit.

35. The surgical device system of claim 31, wherein data from the at least one nonintrusive sensor enables the adaptive flow rate control system to determine fluid velocity, fluid density or fluid temperature.

36. The surgical device system of claim 31, wherein the adaptive flow rate control system further comprises a clog tracking module configured to track a location of a clog within the aspiration conduit, wherein the clog tracking module comprises a plurality of nonintrusive sensors positioned along the aspiration conduit for tracking a location of a clog within the aspiration conduit.

37. The surgical device system of claim 31, wherein the adaptive flow rate control system further comprises a user input receiver configured to receive at least one input from a user to actuate a clog removal function whereby the adaptive flow rate control system is configured to actuate the aspiration pump to increase in speed to create a greater vacuum.

38. The surgical device system of claim 31, wherein the adaptive flow rate control system further comprises a roller valve positioned in the handheld surgical device enabling a user to control aspiration through the aspiration conduit via rotational movement of the roller valve and wherein the adaptive flow rate control system is configured to sense the aspiration reduction caused by movement of the roller valve and send a signal to the aspiration pump to increase in speed to create a greater vacuum.

39. The surgical device system of claim 31, wherein the adaptive flow rate control system further comprises an interface housing configured to house the nonintrusive sensor and to receive data via wireless communications from the at least one nonintrusive sensor.

40. The surgical device system of claim 31, wherein the adaptive flow rate control system further comprises a communication system configured to receive data from the at least one nonintrusive sensor and transmit the data to at least one surgical console configured to control operation of at least one component of the system.

41. The surgical device system of claim 31, wherein the at least one nonintrusive sensor is a camera configured to capture images of matter flowing within the aspiration conduit.

* * * * *